United States Patent [19]

Lee et al.

[11] Patent Number: 5,427,944
[45] Date of Patent: Jun. 27, 1995

[54] BIOREMEDIATION OF POLYCYCLIC AROMATIC HYDROCARBON-CONTAMINATED SOIL

[76] Inventors: Sunggyu Lee, 975 Kingswood Dr., Akron, Ohio 44313; Teresa J. Cutright, 2884 Unclmorse Ave., Akron, Ohio 44314

[21] Appl. No.: 248,373

[22] Filed: May 24, 1994

[51] Int. Cl.$^6$ ........................... C12P 39/00; C02F 3/34
[52] U.S. Cl. ............................ 435/262.5; 435/42; 435/252.4; 435/262; 435/824; 435/863
[58] Field of Search ................. 435/42, 824, 252.4, 435/262.5, 262, 863

[56] References Cited

U.S. PATENT DOCUMENTS

| | | |
|---|---|---|
| 3,300,405 | 1/1967 | Black . |
| 3,871,957 | 3/1975 | Mohan et al. . |
| 4,349,633 | 9/1982 | Worne et al. ......................... 435/281 |
| 4,450,908 | 5/1984 | Hitzman . |
| 4,511,657 | 4/1985 | Colaruotolo et al. . |
| 4,554,075 | 11/1985 | Chang et al. . |
| 4,655,926 | 4/1987 | Chang et al. . |
| 4,761,376 | 8/1988 | Kulpa et al. . |
| 4,765,902 | 8/1988 | Ely et al. . |
| 4,803,166 | 2/1989 | Kulpa et al. . |
| 4,962,034 | 10/1990 | Khan . |
| 4,992,174 | 2/1991 | Caplan et al. . |
| 5,017,289 | 5/1991 | Ely et al. . |
| 5,030,591 | 7/1991 | Cole et al. . |
| 5,059,252 | 10/1991 | Renfro, Jr. . |
| 5,080,782 | 1/1992 | Caplan et al. . |
| 5,098,481 | 3/1992 | Monlux . |
| 5,100,455 | 3/1992 | Pinckard ............................... 71/9 |
| 5,114,568 | 5/1992 | Brinsmead et al. . |
| 5,264,018 | 11/1993 | Koenigsberg et al. .................. 71/63 |
| 5,334,312 | 8/1994 | Lajoie ................................. 210/610 |

*Primary Examiner*—Herbert J. Lilling
*Attorney, Agent, or Firm*—Hudak & Shunk Co.

[57] ABSTRACT

A mixed bacteria culture for biodegrading polycyclic aromatic hydrocarbon contaminants includes Achromobacter sp. and Mycobacterium sp. which have been grown together and gradually acclimated to utilize polycyclic aromatic hydrocarbons as a primary food source. The mixed bacteria culture can be utilized for in situ or ex situ bioremediation of contaminated soil, or in any of various conventional bioreactors to treat contaminated liquids such as landfill leachates, groundwater or industrial effluents. The bacteria, the nutrients used to sustain growth of the bacteria, and the products of the biodegradation of the polycyclic aromatic or other hydrocarbons are all substantially harmless to the environment. The mixed bacteria can be utilized in the presence of oxygen, or hydrogen peroxide can be used alone or in combination with oxygen as an effective alternative electron acceptor. The mixed bacteria culture of Achromobacter sp. and Mycobacterium sp. provides an environmentally safe and affordable means for rapidly and effectively eliminating a variety of polycyclic aromatic hydrocarbon contaminants from the environment.

7 Claims, No Drawings

BIOREMEDIATION OF POLYCYCLIC AROMATIC HYDROCARBON-CONTAMINATED SOIL

FIELD OF INVENTION

The invention relates generally to the remediation of materials which have been contaminated with hazardous substances. More particularly, the invention relates to bioremediation of soil, groundwater, and various waste effluents containing polycyclic aromatic hydrocarbons.

BACKGROUND

Over the past several decades worldwide production, processing, storage, transportation and utilization of synthetic and naturally occurring chemical substances has led to the introduction of significant quantities of hazardous materials into the environment. Unintentional spillage of petroleum distillates, industrial solvents and other chemical substances has been caused, for example, by weathering, chemical corrosion and accidental damage to pipes, storage vessels, processing equipment, transportation vehicles, etc. Deliberate acts and carelessness have also contributed to the release of hazardous substances into the environment. The spillage of such materials has resulted in large numbers of polluted sites and enormous volumetric quantities of soil and groundwater which have been contaminated with hazardous substances. Soil contamination can cause extensive damage to the local ecosystem by accumulating in the tissue of animals and plants, and by causing death thereto and/or mutation to the progeny thereof. Such contamination can also present a serious health threat to humans, and, in extreme cases, can render the contaminated area unsuitable for human habitation. In many cases, contaminated sites can pose a danger to adjacent property, such as by entrainment of hazardous substances by local groundwater flow, and local laws frequently mandate remediation prior to the sale or lease of property wherein the soil has been contaminated with hazardous materials.

Various methods have been utilized for the treatment, remediation or disposal of contaminated soil. These methods generally include permanent removal of the contaminated soil to a secure landfill, incineration, indirect thermal treatment, aeration, venting, air sparging and bioremediation. Removal of contaminated soil to landfills is no longer an attractive alternative on account of the high excavation, transportation and disposal costs, and because of the potential for residual liability. Incineration and indirect thermal treatment can be achieved either on-site or off-site, but in either case involves excavation, handling and treatment of substantially all of the contaminated soil as well as significant amounts of soil adjacent to the contaminated soil. The soil must then either be transported to the treatment facility or else the treatment apparatus must be installed on-site. In either case, these methods generally involve enormous transportation and handling costs, and require large amounts of energy to combust or volatilize the contaminants. Other elaborate and expensive techniques which have been utilized involve excavation and treatment of the contaminated soil using multistep unit operations for separating and recovering the soil from the contaminants. Removal, incineration, indirect thermal treatment and other methods of handling contaminated soil which involve complete excavation of the contaminated soil have the advantage that they can be accomplished in a relatively short amount of time. These methods are particularly attractive in those situations where there is a substantial risk that the contamination will rapidly spread to adjacent property, however, in most cases such methods are prohibitively expensive.

Aeration, venting and air sparging are in situ techniques for removing volatile hazardous contaminants from the soil while simultaneously drawing oxygen into the contaminated soil to enhance biodegradation. Effective removal of hazardous materials by evaporation is generally limited to contaminants having a relatively high vapor pressure. In general, compounds such as polycyclic aromatic hydrocarbons, which have a low-vapor pressure, cannot be successfully removed by volatilization. Moreover, conventional bioremediation techniques utilizing indigenous microorganisms alone or in combination with naturally occurring or genetically altered exogenous microorganisms is not always effective for degrading certain types of recalcitrant contaminants, such as polycyclic aromatic hydrocarbons, which are strongly resistant to biodegradation on account of their polynuclear chemical structure and low concentration in the natural environment.

Thus, while various known techniques are available for the disposal or reclamation of contaminated soil, such methods do not generally provide a practical, affordable technology for remediating soil which has been contaminated with significant quantities of polycyclic aromatic hydrocarbons. Accordingly, there is a need for an inexpensive, environmentally acceptable method and means for remediating soil which has been contaminated with polycyclic aromatic hydrocarbons.

SUMMARY OF THE INVENTION

In accordance with the present invention, there is provided a mixed culture of Achromobacter sp. and Mycobacterium sp. which has been found to be especially efficient for effecting rapid biodegradation of polycyclic aromatic hydrocarbons. The invention also relates to methods of cultivating and acclimating a mixed culture of Achromobacter sp. and Mycobacterium sp. for biodegradation of polycyclic aromatic hydrocarbons. In accordance with another aspect of the invention, there are disclosed nutrient solutions which have been found to be effective for cultivating the mixed culture of the invention for preparation of a suitable inoculum, and for sustaining growth of the microorganisms after they have been introduced into soil containing polycyclic aromatic hydrocarbon contaminants. In accordance with a further aspect of the invention, hydrogen peroxide is used as an alternative electron acceptor or oxidant in place of, or to supplement, oxygen.

The mixed culture of the invention can be used for treating soil in situ utilizing any of the well known methods for introducing exogenous microorganisms into the soil along with nutrients and an optional alternative electron acceptor compound. Conventional methods of introducing bioremediating organisms into contaminated soil are described, for example, in U.S. Pat. No. 4,477 570, incorporated by reference herein. Once established, the organisms can utilize the polycyclic aromatic hydrocarbons contained in the soil as a source of carbon and energy, thereby decontaminating the soil in situ. After the polycyclic aromatic hydrocarbons are consumed, the organisms die without leaving any residual deleterious effect on the environment.

The mixed culture of Achromobacter sp. and Mycobacterium sp. can also be used for ex situ treatment of excavated soil such as by mechanical tillage or other conventional methods of breaking and mixing the soil with a suitable inoculum and nutrients in accordance with the invention.

The mixed culture of Achromobacter sp. and Mycobacterium sp. can also be used to treat contaminated liquid streams such as landfill leachates or industrial effluents containing toxic levels of polycyclic aromatic hydrocarbons. For example, the mixed culture of the invention can be utilized in a sequencing batch reactor as part of the stable biomass of the reactor, or in a bioreactor having support media to which the mixed culture of the invention may attach. Contaminated groundwater can also be treated using the mixed culture of the invention in a bioreactor as, for example, in accordance with the methods and apparatus described in U.S. Pat. No. 5,080,782, incorporated by reference herein.

The mixed culture of the invention can, and might desirably, be used in combination with other remediation techniques such as venting or aeration, as well as in combination with other commonly used microorganisms to remove or biodegrade hazardous contaminants other than polycyclic aromatic hydrocarbons which are or might be present in the soil, groundwater, or other material being remediated.

DETAILED DESCRIPTION OF THE INVENTION

It has been discovered that mixed cultures of microorganisms comprising Achromobacter sp. and Mycobacterium sp. achieve a synergistic effect, wherein the two strains of bacteria when utilized together achieve higher rates of biodegradation of polycyclic aromatic hydrocarbons than would be anticipated based on their individual capacities for metabolizing such compounds. Achromobacter sp. and Mycobacterium sp. are each common, readily obtainable bacteria which are individually known for their ability to utilize hydrocarbon materials as a source of carbon and energy. However, Achromobacter sp. and Mycobacterium sp. are neither known for, nor capable of, individually achieving the high rates of biodegradation of polycyclic aromatic hydrocarbons characteristic of the invention. Additionally, neither Achromobacter sp. nor Mycobacterium sp. are generally known for their ability to achieve a synergistic effect when utilized in combination with other microorganisms.

Although other strains may be used to achieve successful soil remediation, American Type Culture Collection (ATCC) strain 21910 for Achromobacter sp. is preferred. Suitable Mycobacterium sp. include ATCC strains 29676, 29677, 33007 and 49153, with 29676 being preferred.

While the mixed bacteria culture of the invention are capable of biodegrading various aliphatic and aromatic hydrocarbons, they are especially useful because of their unusual ability to rapidly metabolize a variety of polycyclic aromatic hydrocarbons. Examples of polycyclic aromatic hydrocarbons which can be biodegraded using the mixed bacteria culture of the invention generally include any of the various aromatic compounds containing multiple ring structures such as pentalene, indene, naphthalene, azulene, heptalene, biphenylene, asym-indacene, fluorene, phenalene, phenanthrene, anthracene, fluoranthene, acephenanthrylene, aceanthrylene, triphenylene, pyrene, chrysene, naphthacore and the like. Polycyclic aromatic hydrocarbons are generally present in and derived from fossil fuels, especially coal and petroleum. Relatively high concentrations of polycyclic aromatic hydrocarbons are found in coal-tar pitch, petroleum and coal-tar naphtha, and various other high-boiling point petroleum fractions, as well as various products derived therefrom including roofing pitch, sealants, road tars, asphalts, pipe coatings, water-proofing materials, dyes, pesticides, paint additives and wood preservatives. A single large spill of such materials containing high concentrations of polycyclic aromatic hydrocarbons can result in serious contamination requiring remediating. Additionally, various fuels, such as kerosene and gasoline, or other substances containing low concentrations of polycyclic aromatic hydrocarbons can have a cumulative effect. For example, a small leak from an underground storage tank, or repetitive small spills, such as can occur at a fueling facility, can cause accumulation and concentration of the less volatile components, thereby requiring remediation to eliminate the polycyclic aromatic hydrocarbons. Potential applications of the invention include soil remediation at manufactured gas plant sites, coke oven sites, petroleum refineries, fuel depots, gas stations, and other industrial sites.

A suitable inoculum of the mixed culture of the invention can be prepared by first growing the individual bacteria on separate agar plates in a conventional manner. After sufficient growth of the individual bacteria is achieved, both bacteria can be transferred to a fresh agar plate for simultaneous growth of both bacteria together in a mixed culture. After the mixed culture exhibits successful growth, it can be transferred to a suitable vessel containing a nutrient solution, and to which a small amount of polycyclic aromatic hydrocarbons are added for acclimation of the bacteria thereto.

A suitable nutrient system for use during the acclimation process should, at minimum include a nitrogen source, such as an ammonium salt, and a phosphorus source, such as an alkali metal phosphate compound. The nutrient system used during the process of acclimating the mixed bacteria culture to polycyclic aromatic hydrocarbon compounds desirably includes a magnesium source, such as a magnesium salt, and can optionally include other nutrients such as sodium, calcium and iron salts. A suitable nutrient system which can be effectively utilized during the acclimation process includes an ammonium salt and a phosphate compound, along with minor amounts of other conventional nutrients, wherein the molar ratio of elemental nitrogen to phosphorus is from about 5:1 to about 15:1, and more preferably from about 8:1 to about 12:1. A particularly preferred nutrient system for use during the acclimation process includes ammonium chloride, from about 5 to about 20 parts by weight of hydrated magnesium sulfate ($M_aSO_4.7H_2O$) per 100 parts by weight of ammonium chloride, from about 5 to about 20 parts by weight of sodium chloride per 100 parts by weight of ammonium chloride, and from about 15 to about 50, and more preferably from about 20 to about 30 parts by weight of monobasic potassium phosphate ($KH_2PO_4$) per 100 parts by weight of ammonium chloride. The foregoing nutrients are dissolved in a suitable amount of water to dissolve the nutrients and combined with appropriate quantities of a suitable initial primary food source and the mixed bacteria culture. A suitable initial primary food source is generally any aliphatic or mononuclear aromatic hydrocarbon containing from about 6 to about 20 carbon atoms. The amount of primary food source used can be readily determined without undue experimentation by those having ordinary skill in the relevant art, and is generally adjusted so that the ratio of elemental carbon to elemental nitrogen available to the mixed bacteria culture is in the range from about 5:1 to about 20:1 and more preferably in the range from about 8:1 to about 12:1. Initially the primary food source is free of or contains very low levels of polycyclic aromatic hydrocarbons. However, during the acclimation process additional nutrients and primary food source which contains ever increasing amounts of polycyclic aromatic hydrocarbons are added. Preferably, the polycyclic aromatic hydrocarbons which are used during the acclimation process are the same as those present in the soil which is to be remediated with the mixed bacteria culture. In particular, it is recommended that the acclimation process be carried out by adding samples of the soil which is to be remediated to the mixed bacteria culture. This process can be duplicated and repeated as necessary to obtain adequate quantities of the acclimated mixed bacteria culture for preparation of suitable inocula for remediation of soil at or from a contaminated site.

The acclimated mixed bacteria culture of the invention can be introduced, along with suitable nutrients, into soil which has been contaminated with polycyclic aromatic hydrocarbons using generally any of the known in situ or ex situ bioremediation techniques. The acclimated mixed bacteria culture of the invention can also be utilized in generally any conventional bioreactor, either alone or in combination with other biological materials, to eliminate polycyclic aromatic hydrocarbons from landfill leachates, groundwater, industrial effluents, or other liquid streams containing polycyclic aromatic hydrocarbons.

In situ bioremediation of contaminated soil, using the mixed bacteria culture of the invention, can be achieved in combination with other remediation techniques including venting, aeration and air sparging techniques, and can be used in combination with other exogenous biological materials if desired.

The mixed bacteria culture of the invention can be effectively utilized without forced venting or air sparging even in relatively impermeable soil by adding hydrogen peroxide to the soil along with the inoculum and nutrients. The hydrogen peroxide is utilized by the bacteria as an alternative electron acceptor in place of oxygen. Hydrogen peroxide can be utilized as an alternative to oxygen or to supplement oxygen, as desired, especially in those situations where it is difficult or expensive to provide sufficient oxygen to the soil requiring remediation. Care should be taken not to use excessive amounts of hydrogen peroxide which would kill the bacteria of the mixed culture. A suitable amount of hydrogen peroxide is generally, for example, about 0.1 grams of a solution containing 30 percent hydrogen peroxide by weight for every liter of nutrient solution.

Various ratios of Achromobacter sp. to Mycobacterium are effective and can be used to achieve the desired synergism. However, the ratio of Achromobacter sp. to Mycobacterium sp., on a biomass basis, is desirably from about 10:1 to about 1:10, preferably from about 5:1 to about 1:5, and most preferably from about 2:1 to 1:2.

The mixed culture of the invention has been found to be highly effective for rapidly metabolizing and eliminating a wide variety of polycyclic aromatic hydrocarbons. The mixed culture and methods of the invention have the additional advantage of being totally innocuous to the environment. The bacteria and nutrients have no adverse effect on the ecosystem either during or after the remediation process. The bacteria generally die, or at least their population is reduced to a minuscule level, after the hydrocarbons in the soil are consumed. Any hydrogen peroxide, if used, which is not consumed by the mixed bacteria culture of the invention or by other indigenous or exogenous microorganisms, will rapidly decompose into harmless products. The hydrocarbon contaminants are completely mineralized by the mixed bacteria culture of the invention, under aerobic conditions, yielding harmless products (e.g. carbon dioxide, water, biomass and salts).

The present invention therefore provides a safe, effective and inexpensive means for eliminating a wide variety of recalcitrant polycyclic aromatic hydrocarbon contaminants from the environment.

A better understanding of the invention will be had by reference to the following examples which illustrate but which do not in any way limit the scope of the invention.

EXAMPLE 1

The two bacteria strains, Achromobacter sp. (ATCC 21910) and Mycobacterium sp. (ATCC 2676), were initially grown on separate agar slants. After one week, both of the bacteria were transferred to the same agar slant with fresh medium. Growth was allowed for one week, and the culture transferred to a fresh agar slant. The mixed culture contained a 50:50 mixture of the two bacteria on a biomass basis. After the mixed culture exhibited successful growth, it was transferred to a 250 mL flask containing a nutrient solution. The nutrient solution consisted of: 2.0 g $NH_4CL$, 0.2 g $MgSO_4.7H_2O$, 0.2 g NaCl, 0.5 g $KH_2PO_4$, and 1 L distilled water. After 24 hrs., 0.1 g of polycyclic aromatic hydrocarbon contaminated soil was added to the flask and placed in a shake oven at 280 rpm and 32° C. Two mL of the bacteria-nutrient-soil solution was used to inoculate fresh nutrient solution after 6 days of growth. After an additional 24 hours, 0.4 g of soil was added to the new flask. This process was continued three more times to acclimate the mixed culture to the contaminated soil. Five mL of the acclimated bacteria solution was transferred to a 250 mL flask containing 40 g of the contaminated soil. The amount of the contaminations contained in the 40 g sample of contaminated soil prior to treatment are set forth in Table I. Twenty-five mL of the supplemental mineral salt solution was added to the flask. The mineral salt solution consisted of: 4 g $K_2HPO_4$, 4 g $Na_2HPO_4$, 0.2 g $MgCl_2$, 2 g $NH_4Cl$, 0.001 g $CaCl_2$, 1.42 g $Na_2SO_4$, 0.001 g $FeCl3$, and 1 L distilled water. Hydrogen peroxide was used as the oxygen source at a concentration of 0.1 g/L nutrient solution. The flask was then placed in the shake oven at 280 rpm and 32° C. At the end of each week, one flask was removed and dried for analysis. Five mL of the mineral salt solution was added to the remaining flasks. This was repeated for eight weeks. The results are shown in Table I.

TABLE I

| Compound | Contaminant Weights (μg) | | | | |
|---|---|---|---|---|---|
| | Un-treated | Week 3 | Week 4 | Week 6 | Week 8 |
| Acenaphthylene | 0.6538 | — | — | — | — |
| Phenanthrene | 0.0487 | 0.0365 | — | — | — |
| Anthracene | 0.0722 | 0.166 | — | — | — |
| Fluoranthene | 0.1470 | 0.2144 | 0.0623 | 0.0735 | 0.0484 |
| Pyrene | 0.0996 | 0.1715 | 0.0457 | 0.0572 | 0.0323 |
| Terphenyl-d14 | 0.5664 | 0.4911 | — | — | — |
| Chrysene-d12 | 0.2009 | 0.3838 | — | — | — |
| Benz(a)anthracene | 0.4213 | 0.2268 | 0.0644 | 0.0848 | — |
| Chrysene | 0.1377 | 0.1546 | 0.0464 | 0.0589 | — |
| Benzo(b)fluoranthene | 0.2703 | 0.3622 | 0.0954 | 0.1127 | — |
| Benzo(k)fluoranthene | 0.0224 | 0.0318 | — | — | — |
| Benzo(a)pyrene | 0.5725 | 0.1058 | — | — | — |
| Indeno(123cd)pyrene | 0.0586 | 0.0133 | — | — | — |
| Total | 3.2714 | 2.3578 | 0.3142 | 0.3871 | 0.0807 |
| % Remediation | — | 27.93 | 90.40 | 88.17 | 97.53 |

EXAMPLE 2

A mixed culture containing a ratio of Achromobacter sp. to Mycobacterium sp., on a biomass basis, of 25:75 was prepared in a manner similar to the procedure described in Example 1. Five mL of the acclimated bacteria solution was transferred to a flask containing 40 g of a highly contaminated soil as set forth in Table II. The results demonstrate that various ratios of the mixed bacteria culture can be utilized for remediating soil, and that the mixed cultures are effective for remediating highly contaminated soils containing large proportions of higher molecular weight polycyclic aromatic hydrocarbon materials.

TABLE II

| Compound | Contaminant Weights (μg) | | | | |
|---|---|---|---|---|---|
| | Un-treated | Week 1 | Week 2 | Week 3 | Week 4 |
| 2-Fluorophenol | 3.9047 | 0.8317 | — | — | — |
| Naphthalene | 4.2668 | 2.8630 | 1.9540 | 1.490 | — |
| Acenaphthylene | 7.6923 | 0.2673 | 0.2540 | 0.270 | 0.0137 |
| Acenaphthene | 1.3267 | 0.9498 | 0.8732 | 0.3596 | 0.2701 |
| Phenanthrene | 0.0745 | 0.0166 | 0.0092 | 0.0064 | — |
| Anthracene | 0.0227 | — | — | — | — |
| Fluoranthene | 0.6577 | 0.1095 | 0.0896 | 0.0769 | 0.0472 |
| Pyrene | 0.4427 | 0.0708 | 0.0592 | 0.0420 | 0.0307 |
| 4-Terphenyl-d14 | 1.5420 | 0.4062 | 0.3660 | 0.1592 | 0.1134 |
| Chrysene-d12 | 1.8755 | 0.1028 | 0.1664 | 0.1704 | 0.1302 |
| Benz(a)anthracene | 0.5483 | 0.0630 | 0.0590 | 0.0543 | 0.0432 |
| Chrysene | 0.3851 | 0.0531 | 0.0498 | 0.0411 | 0.0308 |
| Benzo(b)fluoranthene | 0.6679 | 0.0376 | 0.058 | 0.0624 | 0.0574 |
| Benzo(k)fluoranthene | 0.0423 | — | — | 0.0133 | — |
| Benzo(a)pyrene | 0.0938 | — | — | — | — |
| Dibenz(ah)anthracene | 0.2309 | — | — | — | — |
| Benzo(ghi)perylene | 0.1645 | — | — | 0.0260 | — |
| Indeno(123cd)pyrene | 0.0174 | — | — | — | — |
| Fluorene | 0.2973 | — | — | — | — |
| TOTAL | 24.2531 | 5.5314 | 3.9384 | 2.7716 | 0.7367 |
| % Remediation | — | 77.19 | 83.76 | 88.57 | 96.96 |

EXAMPLE 3

A 75:25 mixture of Achromobacter sp. to Mycobacterium sp. was prepared in a manner similar to the procedures set forth in experiment 1, and 5 mL of the acclimated bacteria solution was transferred to a flask containing 40 g of the contaminated soil used in Example 2. The results, set forth in Table III, indicate that successful remediation of contaminated soils can be achieved using various proportions of Achromobacter sp. and Mycobacterium sp., and is not limited to 50:50 mixtures, but is generally applicable at various ratios.

TABLE III

| Compound | Contaminant Weights (μg) | | | | |
|---|---|---|---|---|---|
| | Un-treated | Week 1 | Week 2 | Week 3 | Week 4 |
| 2-Fluorophenol | 3.9047 | 2.4450 | 1.3791 | 1.0355 | — |
| Naphthalene | 4.2668 | 2.8245 | 1.6508 | 1.3619 | — |
| Acenaphthylene | 7.6923 | 0.5187 | — | — | 0.1745 |
| Acenaphthene | 1.3267 | 1.1940 | 1.0478 | 0.5046 | 0.2699 |
| Phenanthrene | 0.0745 | 0.0075 | 0.0086 | — | — |
| Anthracene | 0.0227 | — | — | — | — |
| Fluoranthene | 0.6577 | 0.1882 | 0.1541 | 0.1005 | 0.0526 |
| Pyrene | 0.4427 | 0.1359 | 0.1160 | 0.0823 | 0.0398 |
| 4-Terphenyl-d14 | 1.5420 | 1.0402 | — | 0.3897 | 0.1573 |
| Chrysene-d12 | 1.8755 | 0.6645 | 0.1731 | 0.4205 | 0.1868 |
| Benz(a)anthracene | 0.5483 | 0.1544 | 0.0939 | 0.1287 | 0.0584 |
| Chrysene | 0.3851 | 0.1081 | 0.0781 | 0.0859 | 0.0351 |
| Benzo(b)fluoranthene | 0.6679 | 0.1264 | 0.0977 | 0.0900 | 0.0417 |
| Benzo(k)fluoranthene | 0.0423 | 0.0317 | 0.0142 | 0.0295 | 0.0064 |
| Benzo(a)pyrene | 0.0938 | — | — | — | 0.0199 |
| Dibenz(ah)anthracene | 0.2309 | 0.1238 | — | — | — |
| Benzo(ghi)perylene | 0.1645 | 0.0743 | — | — | — |
| Indeno(123cd)pyrene | 0.0174 | 0.0056 | — | 0.0042 | 0.0020 |
| Fluorene | 0.2973 | — | — | — | — |
| TOTAL | 24.2531 | 9.6428 | 4.8134 | 4.2333 | 1.0444 |
| % Remediation | — | 60.24 | 80.15 | 82.55 | 95.69 |

While in accordance with the Patent Statutes, the best mode and preferred embodiment has been set forth, the scope of the invention is not limited thereto, but rather by the scope of the attached claims.

What is claimed is:

1. A process for biodegrading polycyclic aromatic hydrocarbon contaminants, comprising the steps of:
   contacting a mixed bacteria culture comprised of Achromobacter sp. and Mycobacterium sp. with a material containing polycyclic aromatic hydrocarbon contaminants in the presence of nitrogen and phosphorous containing nutrients, and oxygen, hydrogen peroxide or both, the ratio of Achromobacter sp. to Mycobacterium sp., on a biomass basis, being from about 10:1 to about 1:10, the ratio of elemental nitrogen to phosphorous in said nutrients being from about 5:1 to about 15:1.

2. The process of claim 1, wherein said nitrogen source is an ammonium salt and said phosphorus source is a monobasic alkali-metal phosphate.

3. The process of claim 1, wherein the contaminated material is soil.

4. The process of claim 1, wherein the contaminated material is a liquid.

5. A method for in situ bioremediation of soil which has been contaminated with polycyclic aromatic hydrocarbons, comprising the steps of:
   introducing into the contaminated soil an inoculum comprised of a mixed bacteria culture of Achromobacter sp. and Mycobacterium sp. which have been acclimated to polycyclic aromatic hydrocarbons by contacting a growing mixed culture of said bacteria with polycyclic aromatic hydrocarbons, along with a nutrients system containing a nitrogen source and a phosphorous source for sustaining growth of the bacteria, the ratio of Achromobacter sp. to Mycobacterium sp. being from about 10:1 to about 1:10 on a biomass basis, the ratio of elemental nitrogen to phosphorous in said nutrient system being from about 5:1 to about 15:1.

6. The method of claim 5, wherein said nitrogen salt is an ammonium salt and said phosphorus source is a monobasic alkali-metal phosphate, and wherein the molar ratio of ammonium salt to phosphate is from about 8:1 to about 12:1.

7. The process of claim 5, wherein hydrogen peroxide is introduced into the soil as an electron acceptor.

* * * * *